US00PP17118P3

(12) United States Plant Patent
Werner et al.

(10) Patent No.: US PP17,118 P3
(45) Date of Patent: Sep. 26, 2006

(54) PEACH TREE NAMED 'GALACTICA'

(50) Latin Name: *Prunus persica*
Varietal Denomination: Galactica

(76) Inventors: Dennis James Werner, 268 Kilgore Hall, Horticultural Science Department, North Carolina State University, Raleigh, NC (US) 27695-7609; Layne Karlton Snelling, 59 Kilgore Hall, Horticultural Science Department, North Carolina State University, Raleigh, NC (US) 27695-7609

( * ) Notice: Subject to any disclaimer, the term of this patent is extended or adjusted under 35 U.S.C. 154(b) by 0 days.

(21) Appl. No.: 11/022,411

(22) Filed: Dec. 27, 2004

(65) Prior Publication Data

US 2006/0143749 P1 Jun. 29, 2006

(51) Int. Cl.
*A01H 5/00* (2006.01)

(52) U.S. Cl. ..... Plt./196

(58) Field of Classification Search ..... Plt./196
See application file for complete search history.

*Primary Examiner*—Kent Bell
*Assistant Examiner*—June Hwu

(57) ABSTRACT

*Prunus persica* (L.) Batsch 'Galactica' is a new and distinct variety of edible peach tree that has the following unique combination of desirable features that are outstanding in a new variety.

1. Flower buds that demonstrate a high level of resistance to cold temperature injury.
2. Firm, white, low acid flesh fruit with excellent flavor and aroma.
3. Heavy and regular bearing of large size fruit, up to 3 inches in axial diameter.
4. Fruit with early maturity, typically early July in North Carolina.
5. Unique saucer-shaped fruit.

6 Drawing Sheets

Latin name of the genus and species: The Latin name of the novel peach tree variety disclosed herein is *Prunus persica* (L.) Batsch.

Variety denomination: The inventive cultivar of *Prunus persica* disclosed herein has been given the variety denomination 'Galactica'.

BACKGROUND OF THE INVENTION

The present invention relates to a new and distinct cultivar of *Prunus persica* (peach) grown as a fruit tree for home use and for commercial agriculture. Peach is typically grown for their edible fruit that are used for fresh consumption, or for home canning.

The new and distinct variety of peach (*Prunus persica* (L.) Batsch) originated as a first generation descendant from a hand pollinated cross of NCN-4 nectarine (non-patented)×a Chinese saucer peach seedling of unknown origin. The NCN-4 parent was used as the female in the hybridization. The original cross was made in 1995 in Raleigh, N.C. The Chinese saucer peach seedling used as a parent is not available in commerce. The NCN-4 parent used in this hybridization was derived from a hand-pollinated cross of 'Contender' (non-patented)×'Fantasia' nectarine (non-patented) made in 1987 at Jackson Springs, N.C. 'Contender' was named and released as a peach cultivar in 1987. 'Fantasia' nectarine was named and released in Fresno, Calif. in 1969.

The seeds resulting from the 1995 controlled hybridization were germinated in a greenhouse at Raleigh, N.C. in the fall of 1995 and planted in the field in spring of 1996 at Jackson Springs, N.C. These trees, growing on their own roots, first produced fruit in 1998, and one seedling, designated NC98-42, was selected for its large, flat (peento shape)

white flesh fruit, attractive red and cream skin color, fruit with high flavor and aroma, early season of ripening, and heavy fruit production. This original plant was growing on its own roots, and demonstrated characteristics identical to those subsequently expressed when propagated on 'Lovell' seedling rootstock.

Plants and fruit of this new variety differ from its parents. The new variety produces white flesh fruit that are larger, more attractive, earlier in ripening, and firmer than the Chinese saucer peach parent. Fruit of this new peach variety demonstrate the flat, saucer shape character, distinguishing it from the 'Fantasia' nectarine parent. Few saucer shaped (peento) peaches are available in commerce. 'Galactica' ripens 7–10 days later than peento cultivar 'Stark's Saturn' (U.S. Plant Pat. No. 5,123), released in 1985. 'Galactica' has different flesh color (white vs. yellow) and higher flower bud chilling (dormancy) requirement (800 hours vs. 250 hours) than peento cultivar 'UFO' (U.S. Plant Pat. No. 13,352), released in 2002.

During the year 1999, the original plant selection was propagated asexually by grafting of vegetative buds onto the standard peach seedling rootstock cultivar 'Lovell'. Grafting was performed by Mr. Daniel Ferris, at his nursery in Huntland, Tenn. The five trees of the variety grafted by Mr. Ferris were established in test plots in 2000. The new variety has routinely been asexually multiplied by grafting, specifically 'T' budding. It readily forms a graft union with peach 'Lovell' rootstock and resumes normal growth. During all asexual propagation, the characteristics of the original plant have been maintained. Grafted trees on 'Lovell' rootstock exhibit characteristics identical to those of the tree on its own roots, and no aberrant phenotypes have appeared.

Test plantings and performance evaluation over seven years demonstrate this variety to be relatively consistent in its characteristics even under the different growing conditions associated with yearly climatic variation.

Plants of the new variety are very vigorous and grow rapidly after establishment of trees in the field. Young trees have averaged 2–3 feet of growth per year. Plants are semi-upright in growth habit. Flowering sometimes occurs in the second year of growth, but more commonly trees begin flowering and fruiting in the third year after establishment. Flowers are single, medium red-purple, large, and showy. Flowering usually begins in early to mid March in Jackson Springs, N.C.; the chilling requirement is estimated to be 800 hours below 4° C., based on comparison of flowering time to known varieties such as 'Contender' and 'Biscoe'. Flowering generally lasts for 7–10 days, depending on temperature at time of bloom.

Fertility of flowers is excellent, and fruit set is generally very high in most years. Flowers have shown excellent resistance to cold temperatures during winter dormancy and during flower development in the spring. Fruit are very large, often 3 inches in diameter, white fleshed, and highly flavorful and aromatic. Fruit demonstrate the unique saucer shape, often referred to as the "peento" character. Fruit ripen in late June to early July in Jackson Springs, N.C., averaging July 2 over 7 years of observation.

The new variety has been named the GALACTICA cultivar.

SUMMARY OF THE INVENTION

'Galactica' is a new and distinct variety of edible peach tree that has the following unique combination of desirable features outstanding in a new variety.

1. Flower buds that demonstrate a high level of resistance to cold temperature injury.
2. Firm, white, low acid flesh fruit with excellent flavor and aroma.
3. Heavy and regular bearing of large size fruit, up to 3 inches in axial diameter.
4. Fruit with early maturity, typically early July in North Carolina.
5. Unique saucer-shaped fruit.

BRIEF DESCRIPTION OF THE DRAWINGS

The photographs in the drawings were made using conventional film or digital photography techniques, and show the colors as true as reasonably possible by conventional photography. Colors in the photographs may differ slightly from the color values cited in the detailed botanical description, which accurately describe the colors of the new *Prunus persica* variety. All photographs were taken from trees growing at Jackson Springs, N.C.

DETAILED BOTANICAL DESCRIPTION OF THE VARIETY

Figure 1:
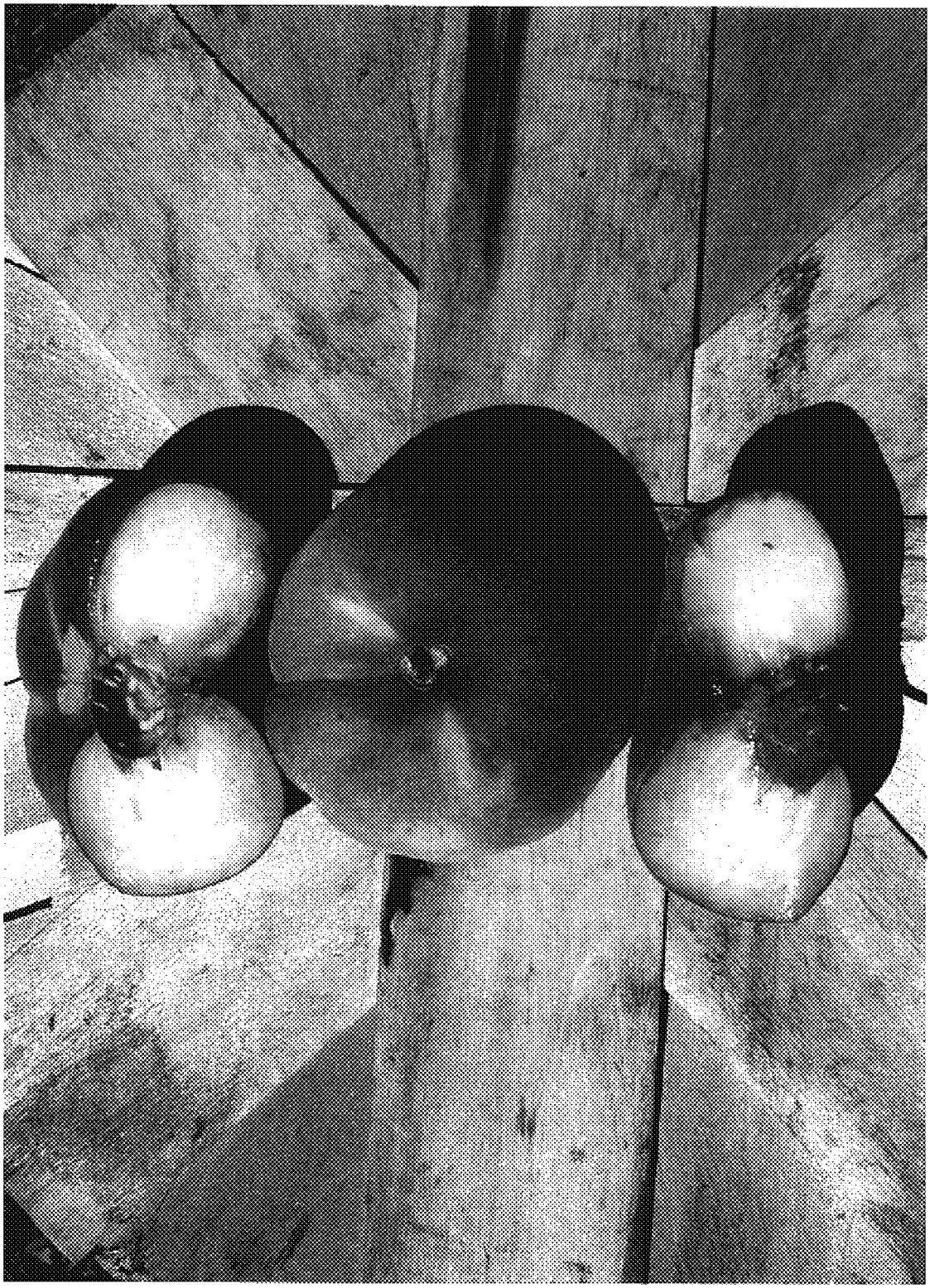
FIG. 1 shows typical fruit of 'Galactica', showing the white flesh with minimal red pigmentation around the stone, and the typical skin coloration.
Figure 2:
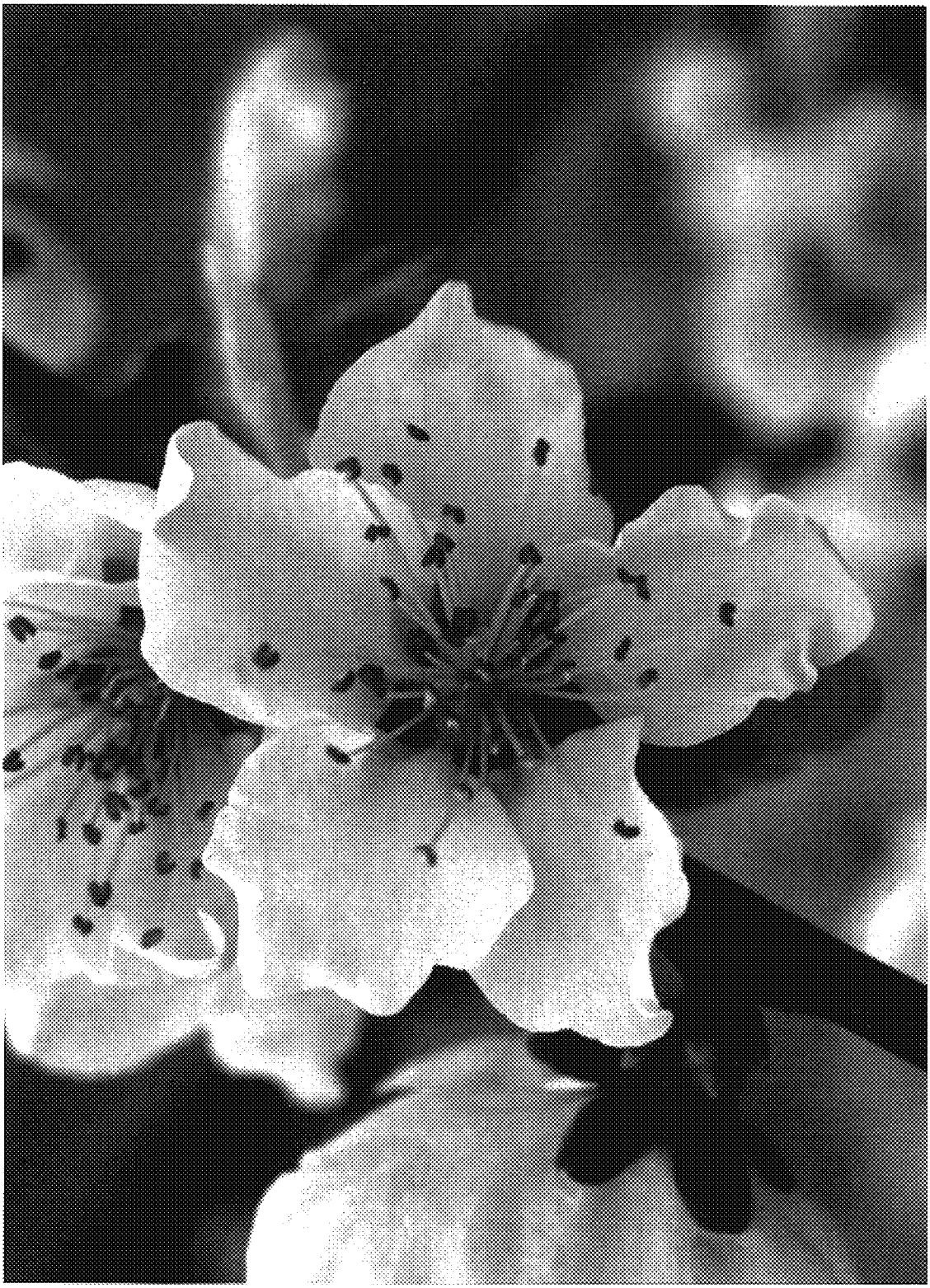
FIG. 2 shows the typical large, showy flower of 'Galactica'.
Figure 3:
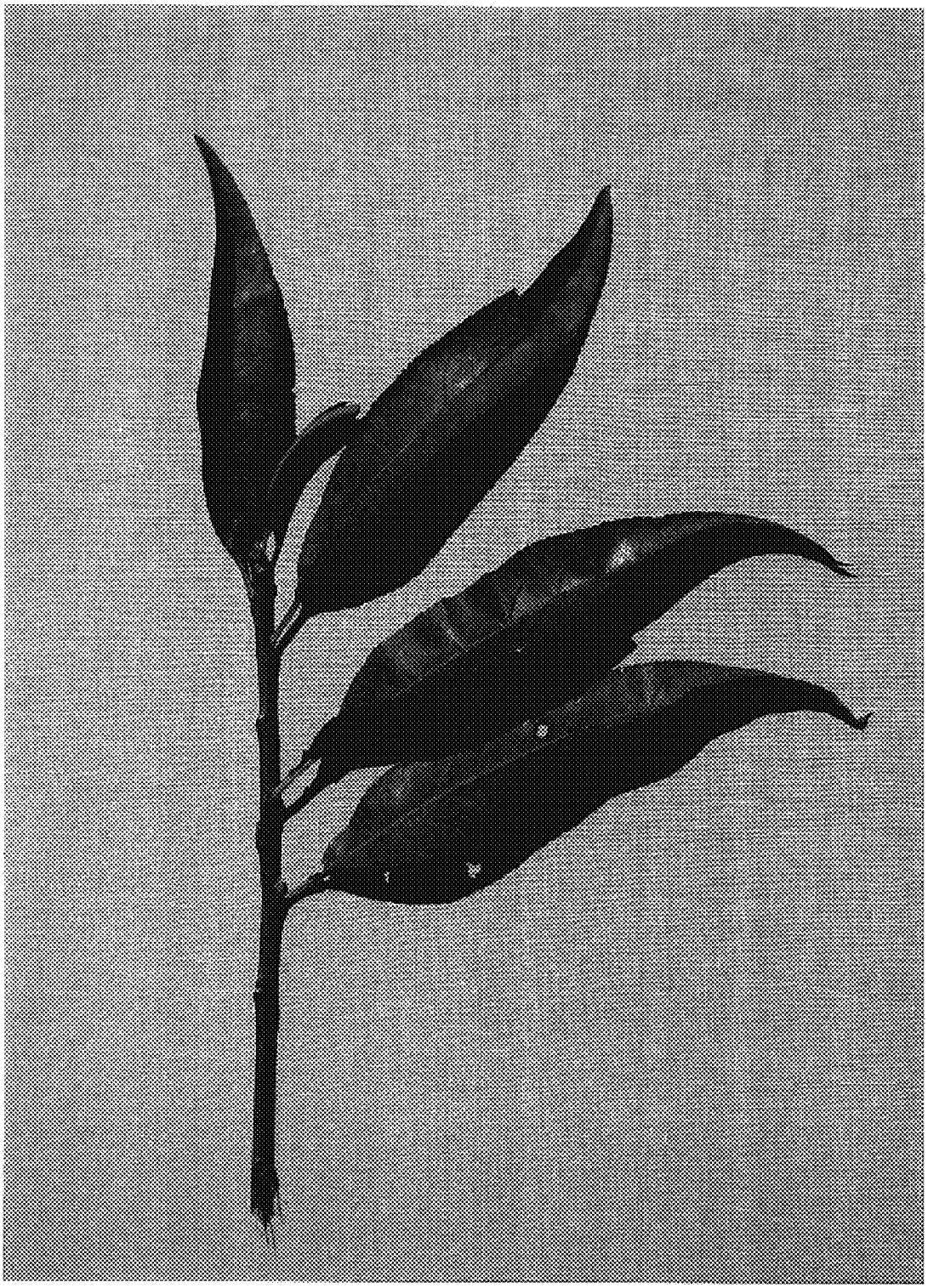
FIG. 3 shows the typical coloration and form of leaves of 'Galactica' taken from a five-year-old tree photographed in September 2004. This figure shows the upper leaf surface.
Figure 4:
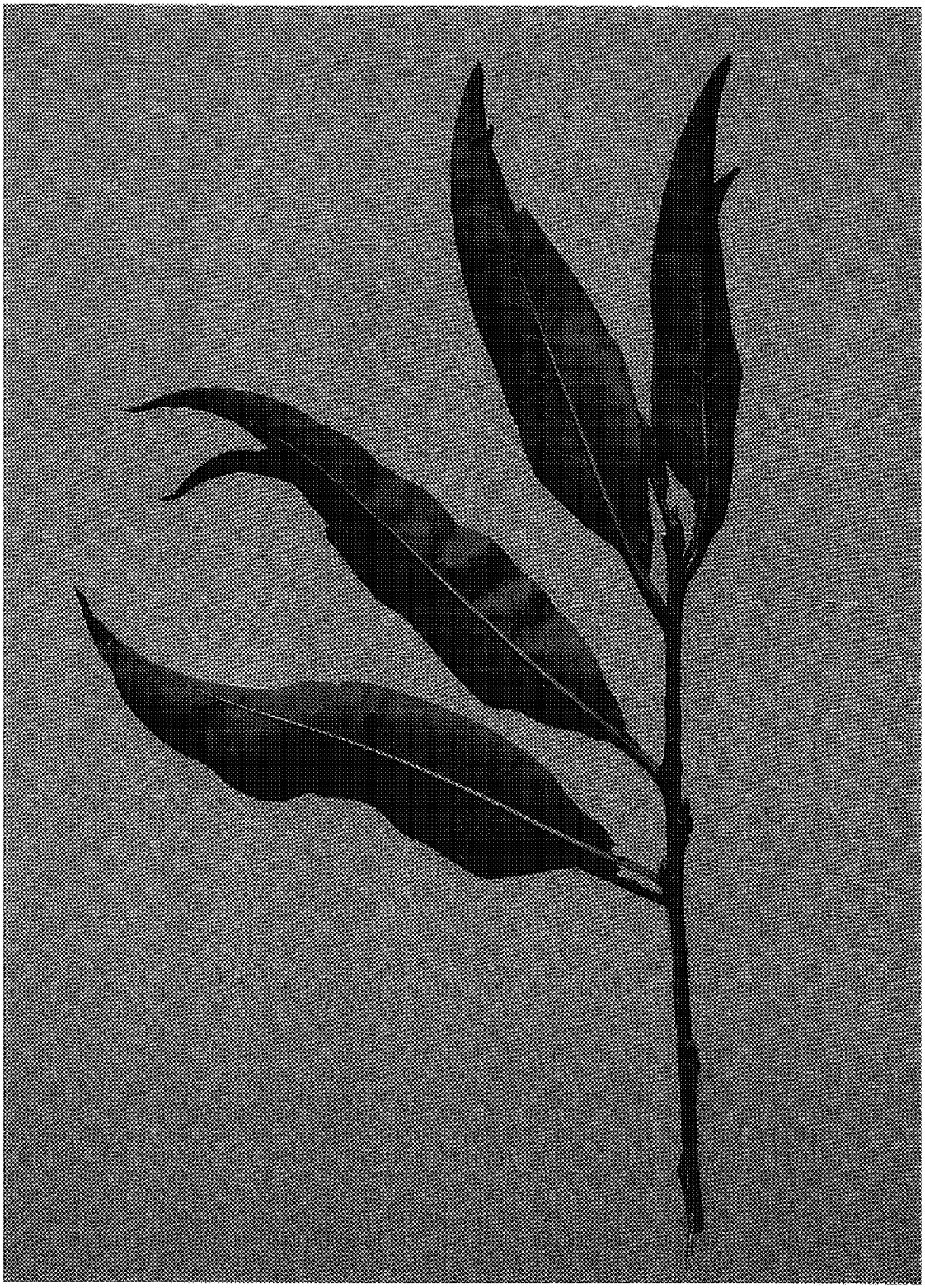
FIG. 4 shows the coloration of the lower leaf surface of leaves of 'Galactica' photographed in September 2004.
Figure 5:
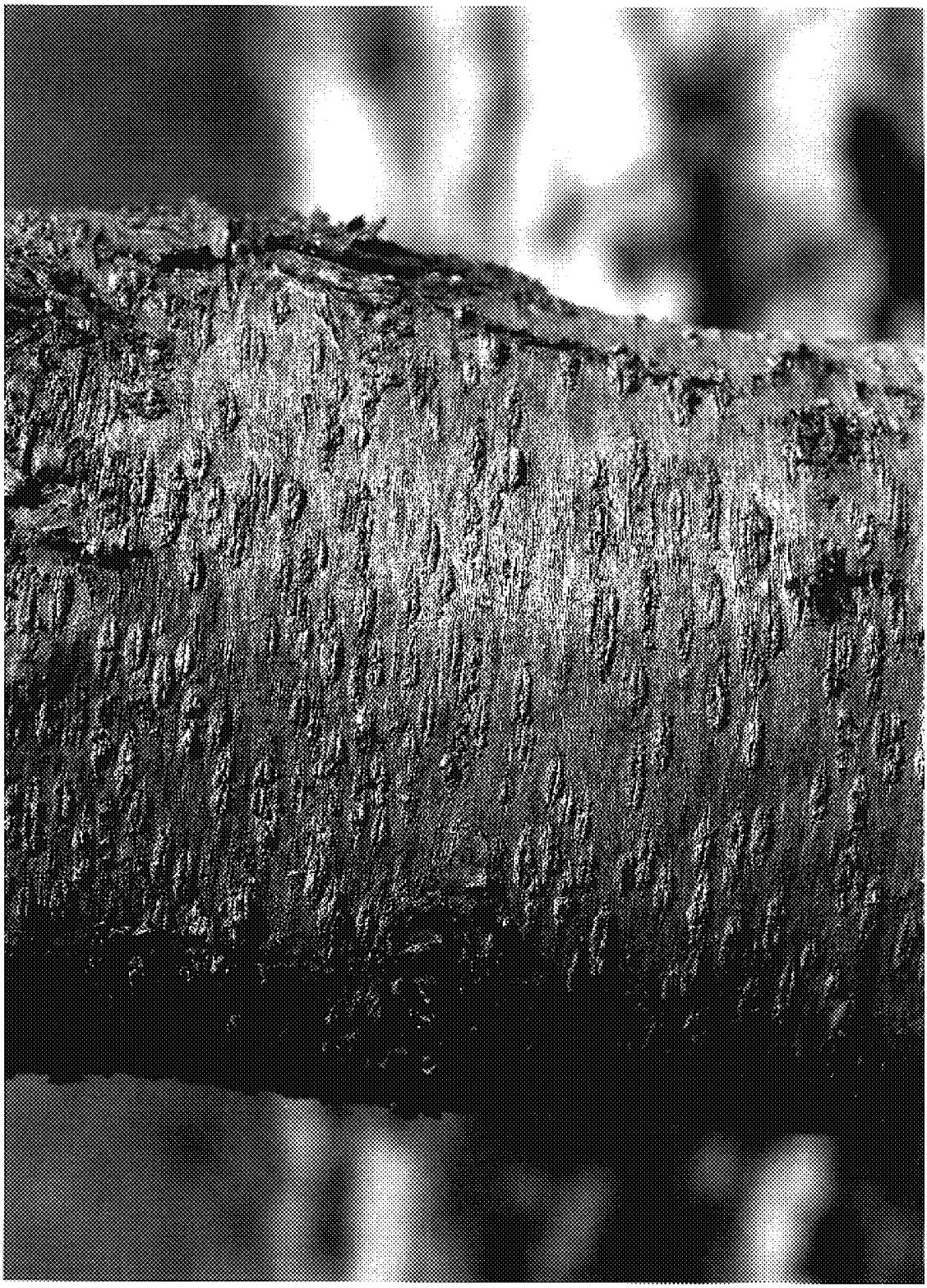
FIG. 5 shows a photograph of the trunk of 'Galactica' taken 1 ft. above the soil line.
Figure 6:
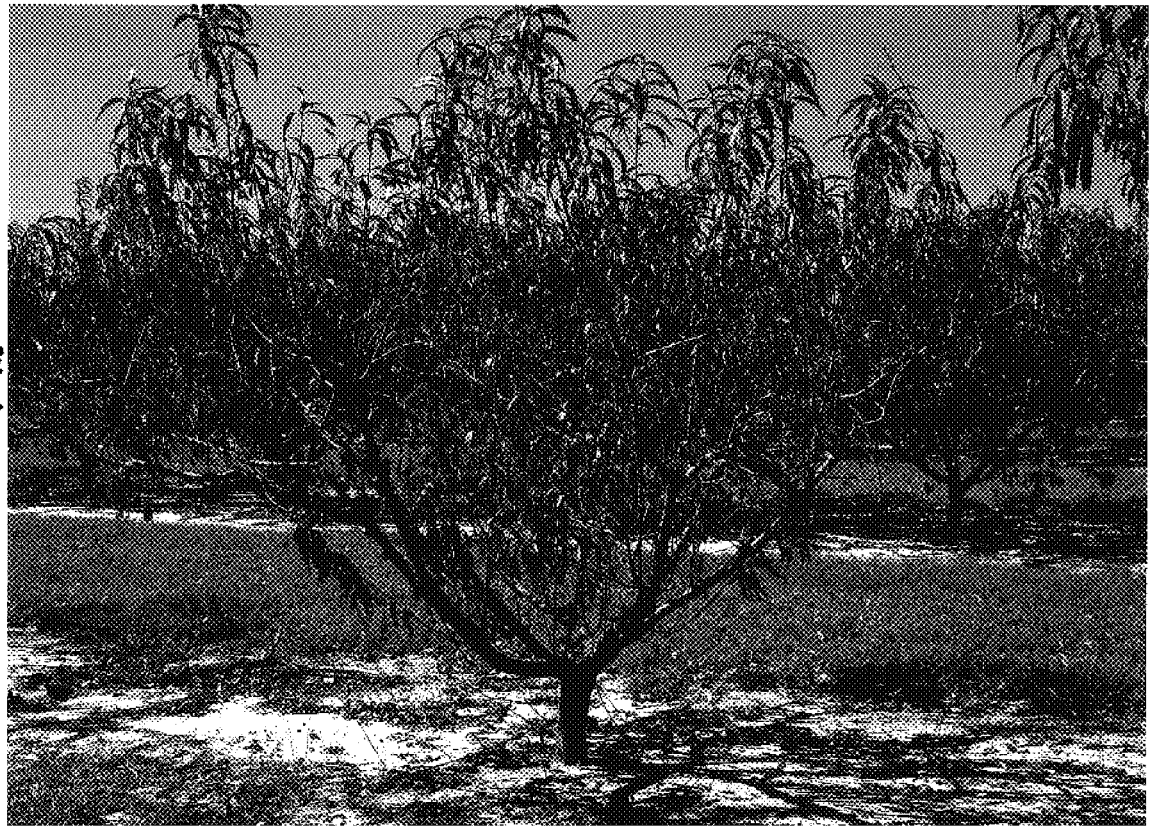
FIG. 6 shows a four-year-old tree of 'Galactica' photographed in September 2004.

The following is a detailed description of the botanical and pomological characteristics of the subject peach. Color data are based on The Royal Horticultural Society Colour Chart, The Royal Horticultural Society, London, 1995 edition. Where dimensions, sizes, colors and other characteristics are given, it is to be understood that such characteristics are approximations of averages set forth as accurately as practicable.

The descriptions reported herein are from four-year-old specimens grown at Jackson Springs, N.C.

Classification: Tree.
Type: Deciduous.
Commercial classification: 'Galactica' serves as a fruit tree that produces high quality peaches for fresh consumption.
Use: Fruit production.
Tree:
- *Size.*—Large. Four-year old tree average height 9.2 ft. Spread 10.0 ft.
- *Vigor.*—Very vigorous.
- *Growth.*—Semi-upright.
- *Production.*—High. Full crop produced yearly in seven years of observation.
- *Hardiness zone.*—Confirmed cold-hardy to USDA hardiness zone 7a. Anticipated to be acceptably cold-hardy to USDA hardiness zone 6. Southern adaptation expected to USDA hardiness zone 8.

Trunk:
- *Size.*—Circumference=13.5 in. (measured 12 inches above soil).
- *Texture.*—Medium to rough.
- *Color.*—Gray-green (RHS 197A).

Branches:
- *Size.*—Medium. Circumference=7.1 in. (measured on main branch at point of attachment to trunk).
- *Surface.*—Smooth (new) to medium rough (old).
- *Lenticels.*—Length=0.9 mm. Width=0.4 mm. Shape=oval. Medium number. Grayed orange (RHS 164C).
- *Color.*—Bright yellow-green (RHS144A, new growth— lower surface), red (RHS46A, new growth— upper surface), grayish-orange (RHS166B, two-year-old branches).

Foliage:
- *Length.*—Large. Mature leaf length 17.1 cm; width 3.9 cm.
- *Form.*—Lanceolate. Acutely pointed.
- *Thickness.*—Medium.
- *Texture.*—Smooth to slightly rugose.
- *Margin.*—Crenate.
- *Petiole.*—Medium length, average=10.6 mm. Color yellow-green (RHS146C).
- *Glands.*—Average number 4. Varies from 3 to 6. Located on base of leaf and upper portion of petiole. Color=RHS144B. Small and reniformis. Length=2.1 mm. Width=1.1 mm.
- *Color.*—Upper surface — yellow green (RHS146A). Lower surface — yellow green (RHS146B).
- *Pubescence.*—Lacking.

Flower buds:

*Size.*—Medium. Typical of peach.

*Width.*—Medium. (3.0 mm).

*Length.*—Medium. (4.2 mm).

*Pubescence.*—Lacking.

*Color.*—Grayed-brown (RHS199B).

Flowers:

*Date of first bloom.*—March 5 to March 15. Varies yearly due to weather conditions.

*Size.*—Large, showy. Diameter=37.0 mm. Varies from 36 to 38 mm.

*Petals.*—Color=medium pink (RHS55C). Length=15.6 mm. Width=14.2 mm. Shape=ovate. Base=rounded. Margin=entire.

*Sepals.*—Color=grayed purple (RHS184A). Length=8.0 mm. Width=3.7 mm. (midsection). Shape=ovate with rounded apex.

*Reproductive organs.*—Stamens — erect, numerous. Average number 40. Ranges from 38 to 42. Filament color — red-purple (RHS63C). Pistils — usually one. Color grayed-yellow (RHS160B). Pollen — normal and abundant, yellow-orange (RHS15A).

*Pollination requirements.*—Flowers self-fertile.

*Number of flowers per bud.*—One.

*Number of petals per flower.*—Average 5.

*Pedicel.*—Long (11.6 mm). Color RHS142C.

*Fragrance.*—None detectable.

Fruit:

*Maturity.*—Early to mid-season. Late June to early July. Average July 2.

*Size.*—Very large. Average 3.1 in. transverse diameter. Average 1.67 in. longitudinal diameter (fruit edge) and 0.9 in. longitudinal diameter (fruit center).

*Weight.*—Average=6.6 ounces.

*Form.*—Flattened.

*Suture.*—Shallow to slightly grooved.

*Pubescence.*—Light to medium.

*Skin color.*—80% red overcolor (RHS34A) with green-white ground color (RHS157B).

*Flesh color.*—Cream white (RHS155C), with slight red intrusion (RHS45B) near the pit.

*Flesh texture.*—Smooth, semi-firm, melting.

*Flesh flavor and aroma.*—Flavor excellent, slight aroma.

*Stone.*—Small, flattened, freestone. Color grayed-orange (RHS175B). Size=1.5 cm. length, 2.0 cm. transverse diameter. Surface texture=rugose. No tendency to crack.

*Pit cavity.*—Width=2.3 cm. Length=1.6 cm. Texture=rugose. Shape=broad, flattened.

*Kernel* (*seed*).—Shape=round, flattened. Color (seed coat)=grayed-orange (RHS163A). Color (seed)=grayed-orange (RHS164D).

*Acidity.*—Semi-acid. pH=4.5 (measured on ripe fruit).

*Soluble solids.*—Average of 5 fruit=14.1 Brix.

*Eating quality.*—Excellent.

*Uses.*—Fresh consumption.

*Browning potential.*—Moderate based on laboratory testing.

Disease reaction:

*Bacterial spot.*—Susceptible based on field observation.

*Peach scab.*—Susceptible.

*Brown rot.*—Susceptible.

Herbarium voucher: A voucher of 'Galactica' will be deposited into the Herbarium of North Carolina State University (NCSU) in Raleigh, N.C., USA upon patenting.

That which is claimed is:

1. A new and distinct variety of peach tree (*Prunus persica* (L.) Batsch) substantially as illustrated and described, characterized by its very large, saucer-shaped, white flesh fruit, semi-acid flesh, high fruit soluble solids, and early ripening time.

* * * * *